(12) United States Patent
Kopf-Sill

(10) Patent No.: US 6,303,343 B1
(45) Date of Patent: Oct. 16, 2001

(54) INEFFICIENT FAST PCR

(75) Inventor: Anne R. Kopf-Sill, Portola Valley, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/287,069

(22) Filed: Apr. 6, 1999

(51) Int. Cl.$^7$ ............... C12P 19/34; C12Q 1/68; C12Q 1/70; C07H 21/02; C07H 21/04
(52) U.S. Cl. ............... 435/91.1; 435/5; 435/6; 435/7.1; 435/21; 435/28; 536/23.1; 536/24.3; 536/24.31; 536/24.32; 536/24.33
(58) Field of Search ............... 435/5, 6, 7.1, 21, 435/28, 91.1; 536/23.1, 24.3, 24.31, 24.32, 24.33

(56) References Cited

U.S. PATENT DOCUMENTS

| | | | |
|---|---|---|---|
| 5,171,132 | 12/1992 | Miyazaki et al. | 417/413 |
| 5,271,724 | 12/1993 | Van Lintel | 417/413.2 |
| 5,277,556 | 1/1994 | Van Lintel | 417/413.2 |
| 5,375,979 | 12/1994 | Hans-Peter Trah | 417/52 |
| 5,498,392 | 3/1996 | Wilding et al. | 422/68.1 |
| 5,587,128 | 12/1996 | Wilding et al. | 422/50 |
| 5,699,157 | 12/1997 | Parce | 356/344 |
| 5,779,868 | 7/1998 | Parce et al. | 204/604 |
| 5,800,690 | 9/1998 | Chow et al. | 204/451 |
| 5,842,787 | 12/1998 | Kopf-Sill et al. | 366/340 |
| 5,852,495 | 12/1998 | Parce | 356/344 |
| 5,869,004 | 2/1999 | Parce et al. | 422/100 |
| 5,876,675 | 3/1999 | Kennedy | 422/99 |
| 5,880,071 | 3/1999 | Parce et al. | 204/453 |
| 5,882,465 | 3/1999 | McReynolds | 156/285 |
| 5,885,470 | 3/1999 | Parce et al. | 216/33 |
| 6,045,993 * | 4/2000 | Mahony et al. | 435/5 |
| 6,180,372 | 1/2001 | Franzen | 435/91.1 |

FOREIGN PATENT DOCUMENTS

| | | |
|---|---|---|
| WO 94/05414 | 3/1994 | (WO) . |
| WO 96/04547 | 2/1996 | (WO) . |
| WO 97/02357 | 1/1997 | (WO) . |
| WO 98/00231 | 1/1998 | (WO) . |
| WO 98/02728 | 1/1998 | (WO) . |
| WO 98/05424 | 2/1998 | (WO) . |
| WO 98/17910 | 4/1998 | (WO) . |
| WO 98/22811 | 5/1998 | (WO) . |
| WO 98/45481 | 10/1998 | (WO) . |
| WO 98/45929 | 10/1998 | (WO) . |
| WO 98/46438 | 10/1998 | (WO) . |
| WO 98/49548 | 11/1998 | (WO) . |
| WO 98/55852 | 12/1998 | (WO) . |
| WO 98/56956 | 12/1998 | (WO) . |
| WO 98/00705 | 1/1999 | (WO) . |
| WO 98/00707 | 1/1999 | (WO) . |
| WO 99/00649 | 1/1999 | (WO) . |
| WO 99/10735 | 3/1999 | (WO) . |
| WO 99/12016 | 3/1999 | (WO) . |
| WO 99/16162 | 4/1999 | (WO) . |
| WO 99/19056 | 4/1999 | (WO) . |
| WO 99/19516 | 4/1999 | (WO) . |
| WO 99/29497 | 6/1999 | (WO) . |

OTHER PUBLICATIONS

Porter et al., "Direct PCR sequencing with boronated nucleotides", Nucleic Acids Research, vol. 25 (8), pp. 1611–1617, Aug. 1997.*
Beskin, et al., (1995) Nucleic Acids Research 23(15):2881–2885.
Raja, et al., (1997) Nucleic Acids Research 25(8):1611–1617.
Kopp et al. (1998) *Science*, 280:1046–48.

* cited by examiner

*Primary Examiner*—W. Gary Jones
*Assistant Examiner*—Arun Kr. Chakrabarti
(74) *Attorney, Agent, or Firm*—Matthew B. Murphy; Jonathan Alan Quine; Law Offices of Jonathan Alan Quine

(57) ABSTRACT

Methods of performing fast polymerase mediated reactions are provided. These reactions can be used in an inefficient fashion in the cycles of the polymerase mediated reactions to produce product at a much faster rate than conventional polymerase mediated reaction methods. Integrated systems for performing these methods are also provided.

104 Claims, 1 Drawing Sheet

INEFFICIENT FAST PCR

CROSS-REFERENCES TO RELATED APPLICATIONS

Not applicable

STATEMENT AS TO RIGHTS TO INVENTIONS MADE UNDER FEDERALLY SPONSORED RESEARCH AND DEVELOPMENT

Not applicable

FIELD OF THE INVENTION

This invention is in the field of cyclic polymerase-mediated reactions such as PCR. More specifically, this invention relates to altering the time within which the steps of such reactions are carried out. The methods of this invention are particularly relevant to reactions such as PCR as performed in devices that allow very short cycle times, such as microfluidic devices.

BACKGROUND OF THE INVENTION

PCR and other cyclic polymerase-mediated reactions are standard tools of modern biological research, and are also commonly used for numerous applications including medical diagnostic procedures and forensic applications. PCR is based on three discrete, multiply repeated steps: denaturation of a DNA template, annealing of a primer to the denatured DNA template, and extension of the primer with a polymerase to create a nucleic acid complementary to the template. The conditions under which these steps are performed are well established in the art.

Generally, standard PCR protocols teach the use of a small number of cycles (e.g. 20–35 cycles) which are optimized for maximum efficiency in each cycle, i.e. to ensure that a highest possible percentage of template molecules is copied in each cycle. Typically, this entails cycle times of 1, 2, or more minutes. For example, the standard reference Innis et al., *PCR Protocols, A Guide to Methods and Applications* (Academic Press, Inc.; 1990)("Innis") suggests the following conditions under the heading "Standard PCR Amplification Protocol" (at page 4):

| | |
|---|---|
| Denaturation | 96° C., 15 seconds |
| Primer Annealing | 55° C., 30 seconds |
| Primer Extension | 72° C., 1.5 minutes |

Such times, or longer, are typical in the field. Similar protocols can be found in, e.g. Sambrook et al. (1989) *Molecular Cloning, A Laboratory Manual* (2d Edition), Cold Spring Harbor Press, Cold Spring Harbor, N.Y. ("Sambrook"), which teaches a 6 minute cycle, and Ausubel et al., eds. (1996) *Current Protocols in Molecular Biology*, Current Protocols, a joint venture between Greene Publishing Associates, Inc. and John Wiley & Sons, Inc. ("Ausubel"), which teaches a 5 minute cycle. Accordingly, only up to about 20 or 35 cycles are typically required to generate a detectable and/or isolatable amount of product.

Recently, attempts have been made to shorten the time required for each cycle of a PCR. Such methods often reduce the time by, for example, performing the PCR in devices that allow rapid temperature changes, thereby eliminating much of the time previously required for PCR to "ramp" the temperature of the solution from one stage of the PCR to the next. In addition, it has been recognized that the use of apparatus that allow greater heat transfer, e.g. thin-walled tubes, turbulent air-based machines, also allow the use of shorter cycle times. For example, the RapidCycler™, from Idaho Technologies, Inc. allows relative rapid ramping times between each temperature of a PCR and relatively efficient thermal transfer from the cycler to the samples. Accordingly, the Idaho Technologies Internet site (www.idahotec.com) provides an example of a PCR, wherein 30 cycles were completed in slightly less than 10 minutes.

Another example was discussed by Kopp et al. (1998) *Science*, 280:1046. Kopp et al. describe a microfluidic continuous flow PCR system where the PCR reactants were flowed through a chip having three discrete temperature zones. A channel was fixed within the chip to allow a fluid within the channel to pass through each of the zones repeatedly, generating a PCR comprising 20 cycles. By varying the speed by which the fluids flowed through the channel, Kopp et al. created a series of PCRs, each with cycles of varying lengths. Because of the design of this system, the reagents within the channel underwent essentially instantaneous changes in temperature. Thus, the cycle time in this system reflected the time at each temperature, with no substantial temporal contribution from the ramping times. Kopp et al. performed a series of 8 reactions, with cycle times varying from 60 to 4.5 seconds.

Consistent with previous studies, the shorter cycles used by Kopp et al. resulted in a significantly decreased amount of product. For example, a cycle time of about 12 seconds generated only about 45% of the product generated by a PCR using a 56 second cycle. A cycle time of 6.6 seconds generated less than about 10% of the 56-second cycle product. A cycle time of 4.5 seconds did not yield any detectable product.

None of these examples have challenged the teaching, well known to those of skill in the art, that regardless of the duration of the cycle, it is desirable to maximize the efficiency of the cycle. Accordingly, even those applications that suggest a low cycle time invariably suggest a standard, low number of cycles. For example, the system used by Kopp et al. was limited to 20 cycles, regardless of the length of the cycle. Similarly, the RapidCycler specifications page suggests using 30 cycle reactions. According to Kary Mullis, the Nobel Prize winning inventor of PCR (as quoted in Innis, supra), "If you have to go more than 40 cycles to amplify a single-copy gene, there is something seriously wrong with your PCR."

This invention is based, in part, on the surprising discovery that it is often desirable to perform PCR using short inefficient cycles. Specifically, despite their relative inefficiency, when short, inefficient cycles are repeated an unconventionally high number of times, it is possible to generate more product in the same amount of time or in less time than under standard conditions.

SUMMARY OF THE INVENTION

This invention is based on the surprising discovery that cyclic polymerase-mediated reactions, such as PCR, can be effectively carried out using very short cycles. As described herein, such reactions can be productively carried out even when the cycles are truncated to the point where they are significantly less efficient than under standard conditions. In particular, this invention demonstrates that performing a cyclic polymerase-mediated reaction using a higher than standard number of such short, inefficient cycles yields a high amount of product. In many cases, the amount of product generated using a high number of short cycles is greater than the amount generated in the same overall amount of time using standard conditions.

This invention teaches methods for performing cyclic polymerase-mediated reactions, wherein template molecules, polymerase enzymes, and primer molecules are incubated so as to extend the primer molecules, thereby duplicating at least a fraction of the template molecules. In these methods, the time allowed for the denaturation of the template and/or extension of the primer is less than under standard conditions, which are generally designed for optimum efficiency, i.e. maximum duplication of the template molecules. Consequently, when performed according to the methods described herein, each cycle of such a reaction is significantly less efficient than is typically accomplished using standard techniques in the art. In preferred embodiments, the percentage of template molecules that are duplicated in the short cycles steps is e.g. 90%, 70%, 50%, 30%, 10%, 5%, or less. Such cycles may be as short as 8–10, 6, 5, 4.5, 4, 2, 1, 0.5 seconds or less.

Because of the relative inefficiency of such short extension steps, the steps are repeated more times than is generally taught according to standard PCR protocols. In certain embodiments, the reaction comprises 30, 50, 70, 100, 200, 400, 1000, or more cycles.

In particularly preferred embodiments of this invention, cyclic polymerase-mediated reactions are performed using a high number of short, inefficient extension steps e.g. in a microfluidic device.

In certain embodiments of this invention, these processes are accomplished by changing the temperature of the solution containing the templates, primers, and polymerase. In such embodiments, the denaturation step is typically accomplished by shifting the temperature of the solution to a temperature sufficiently high to denature the template. In some embodiments, the hybridization step and the extension step are performed at different temperatures. In other embodiments, however, the hybridization and extension steps are performed concurrently, at a single temperature.

In some embodiments, the cyclic polymerase-mediated reaction is performed at a single temperature, and the different processes are accomplished by changing non-thermal properties of the reaction. For example, the denaturation step can be accomplished by incubating the template molecules with a basic solution or other denaturing solution.

Typically, the reactions described herein are repeated until a detectable amount of product is generated. Often, such detectable amounts of product are between about 10 ng and about 100 ng, although larger quantities, e.g. 200 ng, 500 ng, 1 mg or more can also, of course, be detected. In many cases, however, a smaller amount of product is produced, for example, if a detection system is used that can detect less than 10 ng of product. In other cases, a larger amount of product is generated, for example if the product is to be isolated and purified for a separate, product-intensive application. In terms of concentration, the amount of detectable product can be from about 0.01 pmol, 0.1 pmol, 1 pmol, 10 pmol, or more.

The templates used in this invention can be derived from any of a number of different sources, including humans, mammals, vertebrates, insects, bacteria, fungi, plants, and viruses. Often, the templates are about 20–50, 50–100, 100–150, 175, 300, 500, 1000 nucleotides or longer.

The reactions described herein can be used to detect the presence or absence of a template from a sample of interest. Such methods of detection can be used, for example, for diagnostic or forensic purposes. In preferred embodiments, a plurality of samples, each potentially containing a template molecule or molecule, are subjected to the reactions of this invention, in parallel or in series, in order to screen the plurality of samples for the presence or absence of the template.

In certain embodiments, a nucleotide analog is incorporated into the product during one or more cycles of a cyclic polymerase-mediated reaction. Such an analog can be a detectable nucleotide, allowing the detection of the product during or following the reaction using visual or other means. Often, the nucleotide analog allows the sequencing of the product upon its isolation. For example, the analog can be a dideoxynucleotide (or other chain terminating residue) or a boronated nuclease-resistant nucleotide.

This invention also provides apparatus in which to perform the reactions described herein. Such apparatus are generally microfluidic devices. Such devices optionally include elements such as thermal control elements, detection zones, one or more source of test samples, and one or more receptacles for isolating the products of the reactions. In one embodiment, the apparatus is designed to alter the temperature of one or more fluids within the apparatus by joule heating, where the current relative to a cross dimension of a channel is controlled. Such apparatus are optionally part of an integrated system, which can include a computer that controls and/or monitors one or more of the above elements, which stores data, or which selects reaction conditions.

Kits for performing the reactions described herein, in certain cases including the above-described apparatus and integrated systems, instructional materials for practicing the methods herein, and/or packing materials are also provided.

DEFINITIONS

Figure 1:
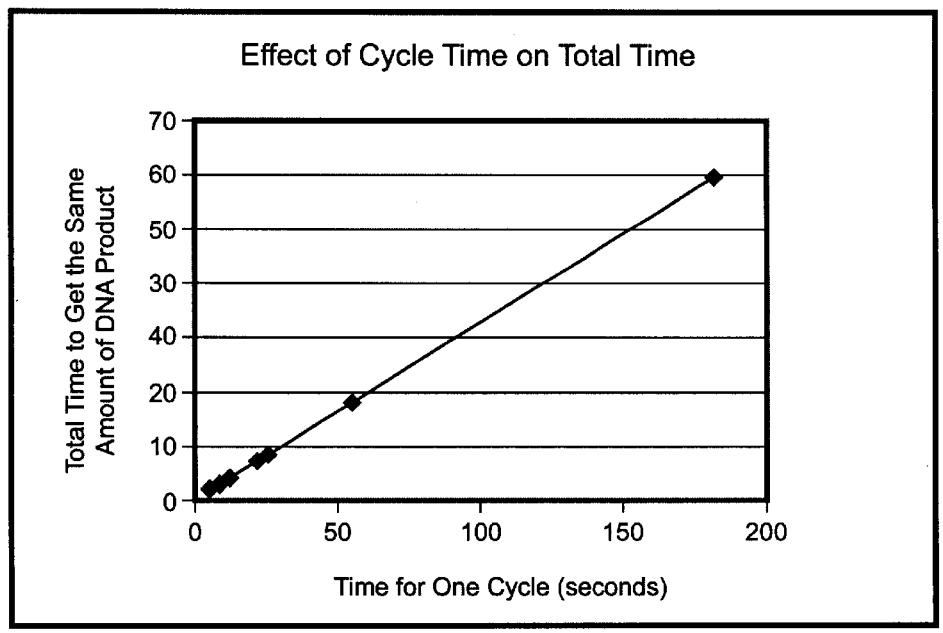
FIG. 1 is a graphical representation of the relationship between the total time required in a PCR to generate a detectable amount of product and the individual cycle time.

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time. Generally, a "cyclic polymerase-mediated reaction" includes primer molecules that serve to initiate synthesis of the complementary template, a polymerase enzyme that catalyzes the synthesis, and monomeric molecules that make up the template. In each cycle of a "cyclic polymerase-mediated reaction" not every template will necessarily by copied, and each complementary template whose synthesis is initiated in a cycle will not necessarily be completed. In preferred embodiments of this invention, the template and primer molecules are nucleic acids, the monomeric units are nucleotides, and the polymerase is a DNA or RNA polymerase.

A "polymerase" is an enzyme that catalyzes the sequential addition of monomeric units to a polymeric chain, or links two or more monomeric units to initiate a polymeric chain. In preferred embodiments of this invention, the "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule.

A "template molecule" refers to a molecule of specific identity which can serve as a template for the synthesis of a complementary molecule. Most often, a "template molecule" is a polymeric molecule. In preferred embodiments, a "template molecule" is a nucleic acid, e.g. DNA, RNA, a nucleic acid comprising both deoxyribo- and ribonucleotides, or a nucleic acids comprising deoxyribonucleotides, ribonucleotides, and/or analogs and derivatives thereof. In the context of PCR, a "template molecule" may represent a fragment or fraction of the nucleic acids added to the reaction. Specifically, a "template molecule" refers to the sequence between and including the two primers.

The "duplication" of a template molecule refers to the synthesis of a molecule that is complementary to the template molecule. In the context of this invention, "duplication" generally involves an incubation in the presence of a primer molecule, polymerase, and nucleotides. For PCR, "duplication" refers to the synthesis of a nucleic acid that spans the sequence between two primers. Thus, if two primers cover a region that comprises a fragment of a nucleic acid added to a reaction, the duplication refers to the synthesis of the nucleic acid, complementary to the added nucleic acid, that spans the region between the two primers.

When reagents are said to be present in "non-rate limiting amounts," this means that the kinetics of the reaction are not primarily determined by the availability of the reagents. In the course of a PCR, when the primer molecules and the polymerase are present in "non-rate limiting amounts," then the kinetics of an extension step of the PCR will generally be determined by factors such as the enzymatic activity, rate, and processivity of the polymerase, the size of the template, etc.

"PCR" refers to a polymerase chain reaction, which is a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are often performed at distinct temperatures, and in distinct temporal steps. In many embodiments, however, the hybridization and primer extension processes can be performed concurrently.

A "microfluidic device" is an apparatus or a component of an apparatus that has one or more microfluidic reaction channels and/or chambers. Typically, at least one reaction channel or chamber of a microfluidic device has a cross-sectional dimension between about 0.1 µm and about 500 µm.

A "microscale channel" is a channel with a cross sectional dimension between about 0.1 µm and about 500 µm.

"Denaturation" of a template molecule refers to the unfolding or other alteration of the structure of a template so as to make the template accessible to duplication. In the case of DNA, "denaturation" refers to the separation of the two complementary strands of the double helix, thereby creating two complementary, single stranded template molecules. "Denaturation" can be accomplished in any of a variety of ways, including by heat or by treatment of the DNA with a base or other denaturant.

A "single stranded template molecule" refers to a denatured template molecule to which a complementary nucleic acid can bind.

"Hybridization" of two nucleic acids refers to the binding of two complementary, single stranded nucleic acids to form a double-stranded nucleic acid.

The "extension of the primer molecules" refers to the addition of nucleotides to a primer molecule so as to synthesize a nucleic acid complementary to a template molecule. "Extension of the primer molecules" does not necessarily imply that the primer molecule is extended to synthesize a complete complementary template molecule. Rather, even if only a fraction of the template molecule has been copied, the primer is still said to be extended.

A "thermocyclic reaction" is a multi-step reaction wherein at least two steps are accomplished by changing the temperature of the reaction.

A "detectable amount of product" refers to an amount of amplified nucleic acid that can be detected using standard laboratory tools. PCR products can be labeled with a detectable marker, separated electrophoretically, and detected visually or using a standard automated detection system such as the Fluor-S MultiImager System (Bio-Rad laboratories) or the Nucleovision from Nucleotech (San Mateo, Calif.). Generally, a "detectable amount of product" is between about 10 ng and about 100 ng of DNA.

When a template is said to be derived from "humans", "mammals", "vertebrates", "insects", "bacteria", "fungi", "plants", or "viruses", it means that the template comprises a nucleic acid whose sequence represents, or corresponds to, a sequence naturally found in the nuclear or mitochondrial genome of one of these types of organisms. The template may be removed directly from such an organism or from biological material originating in such an organism, or may be obtained otherwise, such as by synthesis using standard laboratory technology to conform to a known sequence.

A "target nucleic acid" refers to a nucleic acid of specific sequence, derived from any of a number of sources, including humans, mammals, vertebrates, insects, bacteria, fungi, plants, and viruses. In certain embodiments, the target nucleic acid is a nucleic acid whose presence or absence can be used for certain medical or forensic purposes such as diagnosis, DNA fingerprinting, etc.

A "detectable marker" refers to a nucleotide analog that allows detection using visual or other means. For example, fluorescently labeled nucleotides can be incorporated into a nucleic acid during one or more steps of a cyclic polymerase-mediated reaction, thereby allowing the detection of the product of the reaction using, e.g. fluorescence microscopy or other fluorescence-detection instrumentation.

A "reagent to allow the sequencing of the product" refers to a nucleotide analog that can be incorporated into a nucleic acid during one or more steps of a cyclic polymerase-mediated reaction and which allows the sequencing of the nucleic acid using methods known to those of skill in the art. For example, dideoxynucleotides or boronated nuclease resistant nucleotides can be incorporated into a nucleic acid, allowing the sequencing of the nucleic acid.

A "separation step" refers to the isolation of an amplified nucleic acid. In certain embodiments, the isolated nucleic acid is used to determine the amount of amplified product or to sequence the amplified product. A "separation step" does not necessarily entail the isolation of all of the amplified product, or that the isolation occurs following a final cycle of the reaction. Instead, a "separation step" can occur at any time during the reaction, and can indicate the isolation of only a fraction of the amplified product.

A "reduced-time cycle" refers to a cycle of a PCR, comprising denaturation, annealing, and hybridization steps, that is of shorter duration than an analogous step under standard reaction conditions. In general, such standard conditions are set to allow the duplication of a high percentage of template molecules. Such standard steps generally last about 1 minute per 1 kilobase of template DNA. The present invention, in contrast, uses a "reduced-time cycle," of shorter duration than under standard conditions, and in which a less-than maximum percentage of template molecules is typically duplicated. A reduced-time cycle is typically on the order of 0.1–10 seconds.

A "full-time cycle" refers to a cycle of a PCR performed under standard reaction conditions, which is designed to allow the maximum duplication of the templates in the PCR. Generally, such "full-time cycles" are on the order of about 1 minute per kilobase of template DNA.

An "increased number of reduced-time cycles" refers to a number of PCR cycles that is greater than a standard number of full-time extension steps. Generally, the "increased number of reduced-time extension steps" is determined by the number of PCR cycles required to generate a detectable amount of product using a reduced-time extension step. Typically, an "increased number of reduced-time extension steps" is at least about 30, but can refer to 50, 100, 200, or more cycles.

A "standard number of full-time extension steps" refers to the number of cycles of a PCR that are generally carried out under standard conditions. For most applications, this number is about 20 to 30, and corresponds to the number of cycles required to generate a detectable amount of product using standard conditions, including a full-time extension step.

A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include, Taq, Tth, Pfu, Vent, deep vent, UlTma, and variations and derivatives thereof.

"*E. coli* pol I" refers to the DNA polymerase I holoenzyme of the bacterium *Escherichia coli*.

The "Klenow fragment" refers to the larger of two proteolytic fragments of DNA polymerase I holoenzyme, which fragment retains polymerase activity but which has lost the 5'-exonuclease activity associated with intact enzyme.

"T7 DNA polymerase" refers to a DNA polymerase enzyme from the bacteriophage T7.

A "thermal control element" refers to an element that can apply or remove heat to one or more locations within an apparatus, or which comprises aspects of the design of the apparatus, such as the configuration and/or geometry of a channel within the apparatus, that affect the temperature of fluids flowing through, or situated within, the apparatus.

A "temperature-controlled zone" refers to a region within a channel whose temperature is monitored and/or controlled. Often, the temperature within a "temperature controlled zone" is regulated by a thermal control element.

DETAILED DISCUSSION OF THE INVENTION

I. Inefficient Fast PCR

This invention relates to the surprising discovery that performing PCR with a large number of short, inefficient cycles allows a greater amount of product accumulation in a given amount of time as compared to PCR under normal conditions. The basis for this discovery lies in the observation that, even though the efficiency of each cycle of a PCR is reduced when a cycle is shortened, as taught in the prior art, performing an unconventionally large number of such shortened, inefficient cycles nevertheless allows the production of a large amount of product in a relatively short amount of time.

The methods of this invention can be used for any medical or research application for which PCR is typically used. For example, the methods provided herein can be used for diagnostic purposes. In such embodiments, a nucleic acid can be amplified and sequenced, where the sequence of the amplified product indicates, e.g. the presence or absence of a disease state. In other embodiments, the presence or absence of an amplified product can indicate the presence of a disease state, or, e.g. the presence of an infective virus or microorganism. In additional embodiments, a number of templates can be amplified, using distinct primer sets, from nucleic acids obtained from a single individual, e.g. to determine the sequence of or to clone a number of different loci from the individual. The methods can also be used to screen, e.g. a number of biological samples for a particular gene or gene sequence. Also, the methods are useful to compare the sequence at one or more loci between a number of individuals within a species, or between species, e.g. for population or phylogenetic studies.

The methods provided herein can be used for any standard use of PCR, including amplifying a sequence for, e.g. use as a probe, assaying experimentally obtained cells or animals to confirm the presence or absence of a particular gene or sequence, isolating a specific sequence from a library, e.g. a cDNA or genomic library, or for performing any type of PCR such as quantitative PCR, RTPCR, hot start PCR, LAPCR, multiplex PCR, touchdown PCR, etc. In many embodiments of this invention, the amplified product is sequenced, as described infra, or cloned using standard molecular biological techniques. See, e.g. Ausubel, Sambrook, supra.

A. Short Cycles

One aspect of this invention is the performance of a PCR using cycles that are much shorter than what is taught in the prior art. Numerous references teach standard cycle times. For example, Innis, supra, teaches a standard cycle time of 2 minutes, 15 seconds (not including the time required, called the "ramping time," to change from one temperature to the next using standard equipment). Other protocols teach standard cycles of 5 or 6 minutes or longer (see, e.g., Sambrook or Ausubel, supra).

The minimum time required for a PCR cycle has typically been based on two factors: (i) the amount of time required at each temperature to ensure a high level of efficiency of the reaction, and (ii), the amount of time required to change from one temperature to another during PCR.

In conventional PCR formats, these two factors are mutually reinforcing. Such formats use thermocycling devices that require a substantial amount of time to change between the different temperatures of the reaction. These long ramping times thus provide a substantial minimum time for each cycle, regardless of the duration of the individual steps of the PCR. Such ramping times thus prevent the performance of a large number of cycles in a practical amount of time. Accordingly, it has been imperative to maximize the efficiency of each cycle.

More recently, alternative thermocycling machines have been developed that are capable of carrying out PCR in less time than using conventional equipment. Such apparatus, e.g. the RapidCycler from Idaho Technologies, Inc., are capable of performing PCR with reduced ramping times, and, in large part because of the enhanced thermal conductivity of the apparatus, with shorter denaturation, annealing, and extension steps. Still, the minimum time suggested by the manufacturers of such equipment is on the order of at least about 20 seconds per cycle. Just the extension step alone is recommended to be at least about 5 seconds, not including the additional time introduced by the ramping towards and away from the target extension temperature.

In contrast to the above, the methods of this invention will typically be performed using a microscale device such as a microfluidic device. See, for example, U.S. Pat. Nos. 5,498, 392 and 5,587,128 to Willingham et al. Such devices have the advantage of allowing virtually instantaneous changes in temperature, thereby removing limitation (ii), above, from consideration. Microfluidic devices thus allow the performance of PCR wherein each step of the cycle lasts only seconds, or fractions of a second. Using such devices, the surprising discovery was made that despite their relative inefficiency, such short cycles are nevertheless efficient enough to produce a large amount of product in a shorter than standard amount of time when repeated a high number of times. According to the methods of this invention, such short cycles may be as short as, e.g., 10 seconds, 7.5 seconds, 6 seconds, 5 seconds, 3 seconds, 1 second, 0.5 seconds, or less. Such cycle times are accomplished using microscale devices, for example by altering the flow rate of a fluid through a channel within a microfluidic device, as described infra, or by modifying the current through the channel, or both.

In brief, as described in more detail supra, temperature cycling can be achieved by flowing the reaction components (e.g., by hydraulic or electrokinetic forces) into different regions of a microfluidic system which are maintained at different temperatures. Because of the small volumes of reagents which are typically flowed in microfluidic systems, the reagents almost instantly conform to the surrounding temperature of the microfluidic system.

Alternately, virtually instantaneous heating of reagents in a microfluidic conduit can be achieved by altering the current, voltage, or resistance in a region of a microfluidic conduit. For example, narrowing the diameter of the fluid path increases the resistance in the narrowed region of the fluid path, thereby increasing resistive heating in this region of the conduit. Similarly, increasing the potential difference applied across the length of a channel will increase the amount of current flowing between the regions of potential difference, thereby increasing resistive heating in the conduit. Because the volume of reagent is small, virtually instantaneous cooling of heated reagents can be achieved by reducing resistive heating of the reagents and allowing the reagents to equilibrate with respect to temperature with the microfluidic system. A variety of "joule heating" schemes for PCR in microfluidic systems are taught in WO 98/17910 and in WO 98/45481.

1. Short Denaturation Steps

The efficiency of a cyclic polymerase-mediated reaction can be limited by any of a number of steps within each cycle, including the denaturation step. In PCR, during the denaturation step, the template molecules are heated to a temperature sufficient to separate the two strands of the DNA double helix, thereby allowing the subsequent hybridization of a primer molecule to a single stranded template molecule.

The efficiency of a PCR depends in large part on the efficiency of the denaturation step. Typically, only those template molecules that are completely denatured are successfully copied. Partial denaturation, as may occur in a very short denaturation step as provided herein, can allow the reannealing of the partially denatured strands and the consequent prevention of annealing of the primer to the template.

The efficiency of the denaturation step depends to a large extent on the length of time the template molecules are held at the higher temperature. Typically, such denaturation steps are 15, 30, 60 seconds, or longer, depending in part on the temperature at which the denaturation is carried out. See, e.g. Innis, Sambrook, Ausubel, all supra. Other, more recent references, have taught the use of a denaturation step of as little as one second, using appropriate equipment (e.g. the RapidCycler, supra). In all of the above, the denaturation steps are designed for the maximum denaturation of the templates in each cycle.

It has been discovered that it is desirable to perform PCR even when an extremely short (i.e. less than one second), inefficient denaturation step, for example as performed in a microfluidic device, when the PCR comprises a very high number of cycles. In certain embodiments of this invention, the denaturation step is typically about 0.05–10, e.g., 0.1 to 5, e.g., 0.1–3, e.g., 0.25 to 2, e.g., 0.5–5, 3, 2, 1, 0.75, 0.5, 0.25, 0.1 seconds or shorter. In such embodiments, as little as 90%, 70%, 50%, 30%, 10%, 5%, or fewer of the templates may be denatured.

2. Short Annealing Steps

The annealing step can also contribute to the overall efficiency of a PCR cycle. The annealing step is essential for the progress of a PCR, as primer extension does not typically occur except following a primer annealing event. Conventional protocols teach the use of annealing steps of 30 seconds, 60 seconds, or longer. More recent, "rapid" protocols, teach the use of an annealing step of as short as about one second, not including the ramping time wherein the temperature is often close enough to the target annealing temperature for a substantial amount of annealing to occur. Such ramping times are typically at least several seconds long, e.g., the fastest-ramping machines are capable of changing several ° C. per second. According to the methods of this invention, annealing steps are desirably as short as 5, 3, 1, 0.75, 0.5, 0.25, 0.1 seconds, or shorter.

3. Short Extension Steps

The extension step of a PCR is also an important factor in the efficiency of the overall reaction. Once a primer has annealed to a template, it can be extended when incubated under standard conditions. The proper extension of a primer to synthesize a nucleic acid complementary to the template requires a sufficient amount of time. The amount of time generally suggested for an extension step depends on a number of factors, including the rate and processivity of the polymerase, and the length and concentration of the template. Typically, extension steps of from 1 to 3 minutes are taught for templates of up to about 2 kb (see, e.g. Innis, Sambrook, Ausubel, all supra).

Extension steps shorter than as described above are often of reduced efficiency. Even based on the rate of incorporation of the polymerase enzyme, estimated to vary from 35 to 100 nucleotides per second (see, Innis, supra), it is clear that an extension step of very short duration, e.g. less than several seconds, is inefficient, as it generally does not leave enough time to synthesize a complete complementary template nucleic acid. Nevertheless, as described herein, it has been discovered that even such inefficient extension steps are beneficial when repeated a sufficient number of times. According to the methods of this invention, extension steps are often between about 0.1 and 4 seconds or shorter e.g., 0.5 to about 2 seconds, e.g., 4, 2, 1, 0.5 seconds or less. In such embodiments, as little as about 5%–about 90%, e.g., 10%–70%, e.g., 30–50%, or e.g.,, 90%, 70%, 50%, 30%, 10%, 5%, or fewer of the templates may be completely duplicated in any one cycle.

B. Increased Number of Cycles

Typically, a PCR comprises between about 20 and about 35 cycles. In some extreme cases, e.g. when starting with a very low amount of template or when amplifying a template that is inherently inefficiently replicated, such as one containing repeated sequences, the prior art teaches that it may be necessary to use as many as 45 cycles (see, Ausubel, supra). In general, however, a PCR comprises less than about 35 cycles. Such teachings reflect the fact that PCR conditions are designed to achieve a high efficiency. Accordingly, with a high efficiency, 20–35 cycles are sufficient to generate a large amount of product. In fact, the art teaches that PCR should only be performed using such standard number of cycles, as an inability to generate enough product in 20–35 cycles reflects an inherent problem with the reaction, such as poorly designed primers, a missing component of the reaction, suboptimal magnesium concentration, etc.

TABLE I

| Efficiency | Cycle Time (sec) | No. Cycles |
|---|---|---|
| 2.0 | 60 | 20 |
| 1.4 | 30 | 40 |
| 1.19 | 15 | 80 |
| 1.09 | 7.5 | 160 |
| 1.0443 | 3.75 | 320 |

As shown in Table 1, performing a reaction using a cycle time of 60 seconds, with a relative efficiency of 2.0 (i.e. complete duplication of the templates) produces the same amount of product in the same amount of time as using a cycle time of 3.75 seconds with an efficiency of 1.04 (ie. 4% duplication): Because it is generally possible to obtain higher efficiencies than those shown in Table 1 for short cycles, the amount produced in the total amount of time can be significantly greater than when using a longer, more efficient cycle. Thus, contrary to the teaching of the prior art, it is advantageous to perform PCR using short, inefficient cycles, as is readily possible using a device such as a microfluidic device.

Table 2 provides information regarding the cycle times, productivity, and efficiency for a PCR performed using a fixed number of short cycles of different lengths.

TABLE 2

Times, efficiencies, and product obtained using various cycle times. See, Kopp et al., (1998) Science, 280:1046.

| Total time | % Product | Cycle time (Sec) | Efficiency | Extra cycles | Total time (Min) for 100% | Total cycles for 100% | ln(x)/t |
|---|---|---|---|---|---|---|---|
| 60 | 100 | 180 | 2 | 0 | 60 | 20 | 0.004 |
| 18.7 | 83 | 56.1 | 1.98 | 0.272 | 18.95 | 20.27 | 0.012 |
| 8.3 | 60 | 24.9 | 1.95 | 0.765 | 8.618 | 20.77 | 0.027 |
| 7 | 72 | 21 | 1.967 | 0.485 | 7.17 | 20.49 | 0.032 |
| 4 | 37 | 12 | 1.903 | 1.545 | 4.309 | 21.55 | 0.054 |
| 3 | 20 | 9 | 1.845 | 2.627 | 3.394 | 22.63 | 0.068 |
| 2.2 | 8 | 6.6 | 1.763 | 4.456 | 2.69 | 24.46 | 0.086 |

In contrast to the above, it has been discovered that it is advantageous to perform a PCR using a number of cycles that is significantly greater than the extreme upper limit taught in the prior art. According to the methods of this invention, PCR is desirably performed with about 35 to about 1000 or more cycles, e.g., 50–400 or more cycles, e.g., 75–100 or more cycles, or e.g., 35, 50, 75, 100, 150, 200, 400, 1000 or more cycles. Such high numbers of cycles are readily performed using the apparatus described herein.

C. Total Reaction Time

It has been discovered that, when using a cycle length that permits the duplication of only an unconventionally low percentage of template molecules, it is possible to generate a greater amount of product over a given amount of time than is possible using standard conditions known to those of skill in the art. This is illustrated in Table 1, which lists a series of cycle times, with corresponding efficiencies, that produce an equivalent amount of product in a given amount of time. The efficiencies are presented as a value between 1 and 2,wherein 1 represents no duplication of the templates, and 2 represents complete duplication of all the templates. Also shown in Table 1 is the number of such cycles that can be performed in a given amount of time, in this case 20 minutes.

As evident in Table 2, despite the decreasing efficiency of cycles with a decreasing cycle time (see, column 4), the total time required to produce the maximum amount of product decreases with decreasing cycle time (see, column 6). This relationship between cycle time and total reaction time is shown graphically in FIG. 1.

Using a large number of short, inefficient cycles, it is possible to produce at least as much if not more product in a given amount of time as it is using conventional long, efficient cycles. Accordingly, in certain embodiments of this invention, the total reaction time is similar to those currently employed by practitioners in the field. In particular, the reaction time may be similar to those used currently with "rapid" protocols such as when using a thermocycler such as a RapidCycler, i.e. close to or slightly less than about 10 minutes. In numerous embodiments, however, the reaction time used in this invention are significantly less than even such short reaction times. The reaction times used herein may be as little as e.g., 15 minutes or less, typically 10 minutes or less, e.g., 0.5–10 minutes, e.g., 1–5 minutes, e.g., 1–3 minutes, or e.g., 10, 5, 3, 1, 0.5 or fewer minutes.

D. PCR Using Maximal ln(x)/t Values

Figure 2:
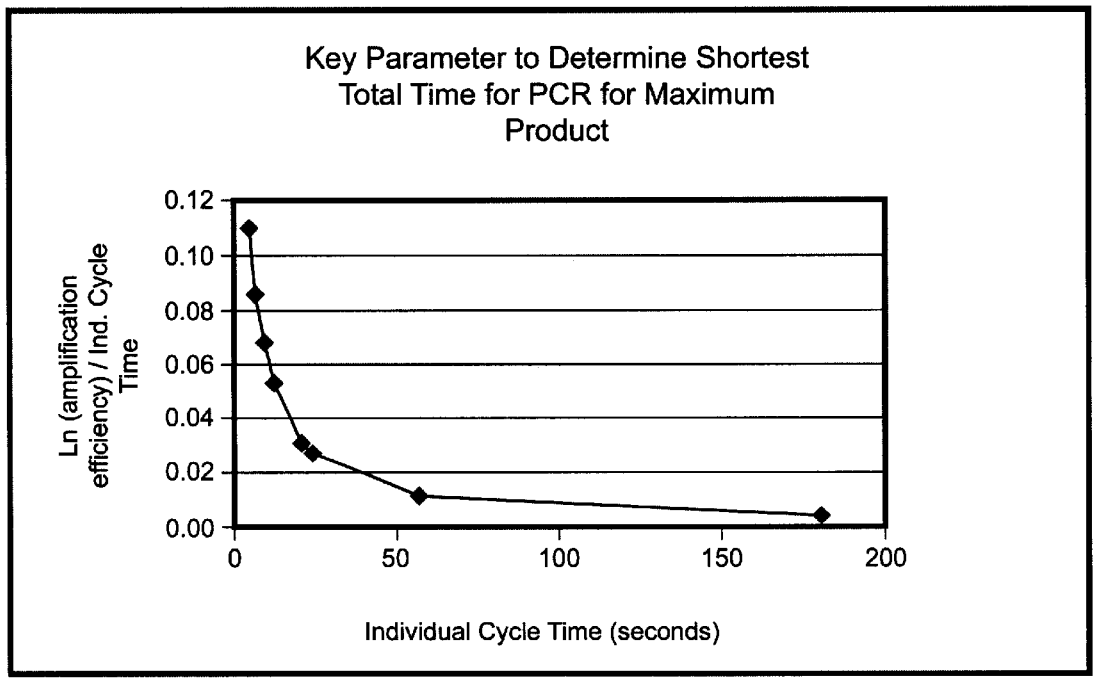
FIG. 2 is a graphical representation of the relationship between ln(x)/t and individual cycle time.

By dividing the natural log value of a cycle efficiency (ln(x)) by the cycle time (t) providing that efficiency (i.e. ln(x)/t), one can determine the relative advantage of performing a PCR using any cycle time. The higher the ln(x)/t value, the more productive the reaction. Conventionally, PCR is performed under conditions where the ln(x)/t is about 0.01 or lower. Under such conditions, the efficiency is at least 1.9 and the cycle time is at least about 90 seconds. In certain cases, such as using newer systems with fast cycle times (e.g. IdahoTec Lightcycler), cycle times of as little as 30 seconds have been recommended. In such cases, the efficiency is still at least about 1.9, and the ln(x)/t value can be around 0.02. In contrast to these conventional methods, however, performing PCR using very short cycle times and an efficiency of as little as 1.7 or less, it is possible to obtain an ln(x)/t value of 0.05, 0.1, or greater. Table 2, supra, shows the relative ln(x)/t for several cycles. ln(x)/t values, relative to individual cycle times, are shown graphically in FIG. 2. As evident in FIG. 2, the ln(x)/t value increases with decreasing cycle time. Even at the lowest value included in Table 2, the ln(x)/t value is still increasing.

II. Reaction Conditions

With the exception of cycle time and number, the methods of this invention can generally be carried out using standard reaction conditions and reagents. Such reagents and conditions are well known to those of skill in the art, and are described in numerous references and protocols. See, e.g. Innis, Sambrook, Ausubel, all supra. Also, see, Mullis et al., (1987) U.S. Pat. No. 4,683,202, and Arnheim & Levinson (Oct. 1, 1990) *C&EN* 6–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564.

A. Thermocyclic Reactions

Cyclic polymerase–mediated reactions such as PCR comprise three overlapping processes: denaturation, primer annealing, and primer extension. For certain reactions, including PCR, such processes are carried out at least 2, and generally 3, or occasionally more than 3, different temperatures. Methods of determining and carrying out such temperatures are well known to those of skill in the art. For example, denaturation steps are often performed at 95°–98° C. Such temperatures will often be used to carry out the present invention. Also, numerous protocols teach the performance of an initial, long denaturation step, particularly when using complex nucleic acids as a starting template, e.g. genomic DNA. In certain embodiments, the present invention will include such initial, longer denaturation steps.

The second process of a cyclic polymerase-mediated reaction is the annealing step, when a primer is hybridized to a denatured template molecule. As known to those of skill, optimal annealing temperatures depend on the melting temperature for the primer and templates, typically falling in the range from about 40° C. to about 65° C. Numerous methods of varying simplicity and precision are known to calculate the melting temperature of nucleic acids. Any such method can be used in the present invention.

Optimal temperatures for the extension step of a PCR are also extensively taught in the prior art. Generally, this temperature is between about 70° C. and about 80° C. Often, the temperature of 72° C. is cited as the ideal temperature for extension. Other temperatures may, however, be used, e.g., depending on the polymerase used, or when performing a PCR wherein the annealing and extension steps are performed simultaneously, as described infra. In such cases, it may be desirable to perform the single annealing/extension step at a temperature intermediate to the ideal temperature for each individual process.

B. Non-thermocyclic

In certain embodiments of this invention, a cyclic polymerase-mediated reaction is performed without changing the temperature of the reactants. In non-thermal amplification, strand separation is optionally carried out by chemical means. In practice, such methods involve the chemical denaturation of nucleic acid strands, followed by dilution or neutralization of the chemical denaturant. For example, in one aspect, strand separation is carried out by raising the pH of the reaction mixture to denature the nucleic acid strands. The pH is then returned to neutral, for annealing and extension. Other chemical denaturants are equally useful to affect strand separation. For example, chaotropic agents, e.g., urea, formamide, and the like, are employed in place of base.

Regardless of the chemical denaturant, however, addition of these materials will typically result in the denaturing of the enzymes present in the reaction mixture, e.g., polymerases, in addition to the nucleic acids, and thereby lead to their inactivation. As such, performance of this type of amplification at the bench scale, would require large amounts of expensive enzymes. Further, the additional volume required for adding these enzymes, as well as diluting or neutralizing the denaturants, would result in cumbersome manipulations, particularly where a large number of cycles is performed. As the methods described herein will most often be carried out using microfluidic devices, however, such problems will not affect the performance of the present invention.

In the systems, devices and methods of the present invention, non-thermal amplification can be carried out by introducing a sample or target nucleic acid into a reaction chamber, channel or zone of a microfluidic device. Methods of performing non-thermal cyclic polymerase mediated reactions are also described in "Closed Loop Biochemical Analyzers" (WO 98/45481). The complementary strands of the target nucleic acid are melted apart by introducing a preselected volume of a chemical denaturant, which denatures the complementary strands of the nucleic acid. In particularly preferred aspects, denaturation is accomplished by raising the pH of the reaction mixture to approximately 10–13. This is readily accomplished by introducing NaOH, (e.g., approximately 0.2N NaOH).

Annealing of the primers to the target strand is carried out by removing the denaturing effects of the denaturant. For example, in those aspects where a dilute base is used to denature the nucleic acid, the base is optionally neutralized by the addition of a similar volume of dilute acid, e.g., 0.2N HCl. Where chaotropic agents are used, the denaturing effect can generally be removed by desalting the reaction mixture or the like. A preselected volume containing an effective amount of polymerase enzyme and primer sequences are then added to the reaction mixture, i.e., sufficient to amplify the target sequence.

Because volumes of reagents are typically small in the devices and methods of the invention, the polymerase need not be thermally or otherwise stable to the more extreme conditions of the amplification reaction as in PCR, i.e. the denaturation of the nucleic acids will often result in the denaturation of the polymerase enzyme as well. However, additional amounts of enzyme can be added back to the amplification mixture. Because small volumes are used, the costs are maintained relatively low. As a result of this, any number of a variety of common polymerase enzymes can be used, including *E. coli* DNA polymerases, e.g., *E. coli* DNA pol 1, Klenow fragment, T7 DNA polymerase or the like. Indeed, one advantage of short cycle times is the fact that non-thermostable enzymes can be used even for thermocyclic reactions. See also, PCT/US98/17910. Further, one could operate the system at an elevated temperature and utilize thermally stable Taq polymerases, Pfu DNA polymerase, Bst and Vent, all of which are commercially available.

C. Number of Steps Per Cycle

In certain embodiments of this reaction, a cyclic polymerase-mediated reaction will comprise two instead of three or more distinct temperature or chemical steps to accomplish the three basic processes of the reaction described supra. Generally, this is done by performing the annealing and primer extension steps concurrently.

For example, in a thermocyclic reaction, following the incubation of the reactants at a high temperature to effect the denaturation of the template molecules, the reactants can be incubated at a temperature that is intermediate to the optimal temperature for either process alone. Often, such temperatures are between about 60° C. and about 72° C.

For non-thermocyclic reactants, wherein the different steps of the reaction are performed at a single temperature, the single temperature can be set at a temperature that allows both annealing and hybridization. Because the chemical requirements are similar for annealing and hybridization, it is generally desirable to perform both of these processes simultaneously. Thus, in preferred embodiments, non-thermal cyclic polymerase-mediated reactions comprise two distinct steps, each comprising a unique chemical environment.

D. Reagents

Reagents for the practice of PCR and related reactions are amply described in the prior art. For example, Innis, Sambrook, and Ausubel, all supra, each provide substantial teaching regarding optimal reagents for PCR. In addition, numerous references on the Internet provide protocols and methods for PCR and related reactions (see, for example, www.alkami.com/or www.promega.com/amplification/prodguide/).

Buffers for PCR and related reactions can be easily made using standard laboratory chemicals according to recipes provided in the above-cited protocols. Alternatively, buffers and additional reagents useful for PCR can be commercially obtained from any of a variety of companies such as BRL, Sigma, Perkin-Elmer, Roche, Boehringer Mannheim, Stratagene, NEB, and others. Such companies and the above references provide substantial guidance for the optimal use of such buffers. Nucleoside triphosphates, often derivatized as described infra, can also be readily obtained commercially. In addition, guidance for their use can be found in any of a multitude of sources including guides such as Innis, Sambrook, Ausubel, etc., product literature from companies, Internet protocols and technical discussion groups, etc. Similarly, other reagents commonly used in cyclic polymerase-mediated reactions such as $Mg^{++}$ ions, BSA, detergents, etc, can be readily obtained and guidance for their optimal use readily found in any of the above sources.

1. Samples/Templates

The templates used in the methods of this invention can be obtained from any source that potentially contains an amplifiable nucleic acid. Such sources include those from any animal, including humans and other mammals, as well as plants, fungi, bacteria, and archaebacteria. Templates can be prepared from any material containing cells or nucleic acids. In the case of an animal, such material includes, e.g. tissue biopsy, blood, hair, buccal scrapes, etc. In the case of plants, such materials include seeds, spores, embryos, flowers, ovules, leafs, stems, etc. Methods for the preparation of templates can be found in a multitude of sources, including Innis, Sambrook, Ausubel, all supra. Any such method can be used in the present invention. Typically, these methods involve cell lysis, followed by purification of nucleic acids by methods such as phenol/chloroform extraction, electrophoresis, and/or chromatography. Often, such methods include a step wherein the nucleic acids are precipitated, e.g. with ethanol, and resuspended in an appropriate buffer for addition to a PCR or similar reaction.

The choice of the template used in the present invention will depend on the particular application used. Any of a large number of such applications exist. Simply put, any nucleic acid desirably amplified may be used in the present invention. Such applications include diagnostic procedures, wherein the presence or absence of a particular nucleic acid provides information regarding the existence or state of a biological condition, such as a disease. In other applications, nucleic acids are amplified for use in a downstream application, such as for use as a probe, or for sequencing, i.e. to determine the precise sequence of a particular genetic locus in one or more individual samples.

In certain embodiments, a plurality of templates from one or more sources are used in the present invention. For example, a single nucleic acid from a multitude of sources may be amplified to screen for the presence or absence of a particular sequence. In other applications, a plurality of nucleic acids may be amplified from a single sample or individual, thereby allowing the assessment of a variety of nucleic acids in a single individual, e.g. to simultaneously screen for a multitude of disease markers in an individual. Any of the above applications can be easily accomplished using the apparatus and integrated systems described herein. For example, in one embodiment, an apparatus comprising a plurality of sources of test samples is used to carry out the present invention.

2. Primers

Oligonucleotides for use as primers, e.g., in PCR or non-thermal amplification reactions, are typically synthesized chemically according to the solid phase phosphoramidite triester method described by Beaucage and Caruthers (1981), *Tetrahedron Letts.,* 22(20):1859–1862, e.g., using an automated synthesizer, as described in Needham-VanDevanter et al. (1984) *Nucleic Acids Res.,* 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

While primers can hybridize to any of a number of sequences, selecting optimal primers is typically done using computer assisted consideration of available sequences and excluding potential primers which do not have desired hybridization characteristics, and/or including potential primers which meet selected hybridization characteristics. This is done by determining all possible nucleic acid primers, or a subset of all possible primers with selected hybridization properties (e.g., those with a selected length, G:C ratio, uniqueness in the given sequence, etc.) based upon the known sequence. The selection of the hybridization properties of the primer is dependent on the desired hybridization and discrimination properties of the primer. In general, the longer the primer, the higher the melting temperature. As noted above, any desired primer can be synthesized using standard methods. In one aspect, microfluidic systems for, e.g. PCR, include pre-made primer sets which are selected for use in the system.

Microfluidic systems utilizing primer sets for, e.g., PCR, are set forth in WO 98/45481. For example, modular primers can be used in the reactions of this invention. See, WO 98/45481 and Beskin et al. (1995) *Nucleic Acids Research* 23(15):2881–2885. See, also, Raja et al. (1997) *Nucleic Acids Research* 25(4):800–805.

In general, it is expected that one of skill is thoroughly familiar with the theory and practice of nucleic acid hybridization and primer selection. Gait, ed. *Oligonucleotide Synthesis: A Practical Approach*, IRL Press, Oxford (1984); W. H. A. Kuijpers *Nucleic Acids Research* 18(17), 5197 (1994); K. L. Dueholm *J. Org. Chem.* 59, 5767–5773 (1994); S. Agrawal (ed.) *Methods in Molecular Biology*, volume 20; and Tijssen (1993) *Laboratory Techniques in biochemistry and molecular biology—hybridization with nucleic acid probes*, e.g., part I chapter 2 "overview of principles of hybridization and the strategy of nucleic acid probe assays", Elsevier, N.Y. provide a basic guide to nucleic acid hybridization. Innis supra provides an overview of primer selection.

One of skill will recognize that the 3' end of an amplification primer is more important for PCR than the 5' end. Investigators have reported PCR products where only a few nucleotides at the 3' end of an amplification primer were complementary to a DNA to be amplified. In this regard, nucleotides at the 5' end of a primer can incorporate structural features unrelated to the target nucleic acid; for instance, in one embodiment, a sequencing primer hybridization site (or a complement to such as primer, depending on the application) is incorporated into the amplification primer, where the sequencing primer is derived from a primer used in a standard sequencing kit, such as one using a biotinylated or dye-labeled universal M13 or SP6 primer.

One of skill will recognize that there are a variety of possible ways of performing the primer selection steps, and that variations on the steps are appropriate. Most typically, selection steps are performed using simple computer programs to perform the selection as outlined above; however, all of the steps are optionally performed manually. One available computer program for primer selection is the MacVector program from Kodak. An alternate program is the MFOLD program (Genetics Computer Group, Madison Wis.) which predicts secondary structure of, e.g., single-stranded nucleic acids. In addition to programs for primer selection, one of skill can easily design simple programs for any or all of the preferred selection steps.

3. Polymerases

Any of a variety of polymerases can be used in the present invention. For thermocyclic reactions, the polymerases are thermostable polymerases such as Taq, KlenTaq, Stoffel Fragment, Deep Vent, Tth, Pfu, Vent, and UlTma, each of which are readily available from commercial sources. Similarly, guidance for the use of each of these enzymes can be readily found in any of a number of protocols found in guides, product literature, the Internet (see, for example, www.alkami.com/), and other sources.

For non-thermocyclic reactions, and in certain thermocyclic reactions, the polymerase will often be one of many polymerases commonly used in the field, and commercially available, such as DNA pol 1, Klenow fragment, T7 DNA polymerase, and T4 DNA polymerase. In applications for RNA amplification, a number of RNA polymerases are also commercially available, such as T7 RNA polymerase and SP6 RNA polymerase. Guidance for the use of such polymerases can readily be found in product literature and in general molecular biology guides such as Sambrook or Ausubel, both supra.

4. Nucleotides

Those of skill in the art are aware of the variety of nucleotides available for use in the present reaction. Typically, the nucleotides will consist at least in part of deoxynucleotide triphosphates (dNTPs), which are readily commercially available. Parameters for optimal use of dNTPs is also known to those of skill, and is described, e.g. in Innis, Sambrook, or Ausubel, supra. In addition, a large number of nucleotide derivatives are known to those of skill and can be used in the present reaction. Such derivatives include fluorescently labeled nucleotides, allowing the detection of the product including such labeled nucleotides, as described below. Also included in this group are nucleotides that allow the sequencing of nucleic acids including such nucleotides, such as dideoxynucleotides and boronated nuclease-resistant nucleotides, as described below. Other nucleotide analogs include nucleotides with bromo-, iodo-, or other modifying groups, which groups affect numerous properties of resulting nucleic acids including their antigenicity, their replicatability, their melting temperatures, their binding properties, etc. In addition, certain nucleotides include reactive side groups, such as sulfhydryl groups, amino groups, N-hydroxysuccinimidyl groups, that allow the further modification of nucleic acids comprising them.

(1) Detectable Markers

In one class of embodiments of this invention, a detectable label is incorporated into a nucleic acid during at least one cycle of the reaction. Such labels can be detected by spectroscopic, photochemical, biochemical, immunochemical, electrical, optical or chemical means. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, $^{32}$P, $^{33}$P, etc.), enzymes (e.g. horse-radish peroxidase, alkaline phosphatase etc.) colorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means.

Polymerases can also incorporate fluorescent nucleotides during synthesis of nucleic acids. See, e.g. Hawkins et al., U.S. Pat. No. 5,525,711, where the use of pteridine nucleotide analogs which are incorporatable by Taq is described.

(2) Sequencing Reagents

Reagents allowing the sequencing of reaction products can be utilized herein. For example, chain-terminating nucleotides will often be incorporated into a reaction product during one or more cycles of a reaction. The most popular chain termination methods of DNA sequencing are variants of the dideoxynucleotide mediated chain termination method of Sanger. See, Sanger et al. (1977) *Proc. Nat. Acad. Sci., USA* 74:5463–5467. For a simple introduction to dideoxy sequencing, see, *Current Protocols in Molecular Biology,* F. M. Ausubel et al., eds., Current Protocols, a joint venture between Greene Publishing Associates, Inc. and John Wiley & Sons, Inc., (Supplement 37, current through 1997) (Ausubel), Chapter 7. Commercial kits containing the reagents most typically used for these methods of DNA sequencing are available and widely used.

In addition to the Sanger methods of chain termination, PCR exonuclease digestion methods for DNA sequencing can be used. For example, direct sequencing of reaction products is provided by selectively incorporating boronated nuclease resistant nucleotides into reaction products during one or more cycles of a reaction. (Porter et al. (1997) *Nucleic Acids Research* 25(8):1611–1617). In such methods, 4 PCR reactions on a template are performed, in each of which one of the nucleotide triphosphates is partially substituted with a 2'deoxynucleoside 5'-[P-borano]-triphosphate. The boronated nucleotide is stochastically incorporated into PCR products at varying positions along the PCR amplicon in a nested set of PCR fragments of the template. Subsequently, an exonuclease which is blocked by incorporated boronated nucleotides is used to cleave the PCR amplicons. The cleaved amplicons are then separated by size using polyacrylamide gel electrophoresis, providing the sequence of the amplicon. An advantage of this method is that it requires fewer biochemical manipulations than performing standard Sanger-style sequencing of PCR amplicons.

In addition to enzymatic and other chain termination sequencing methods, products can be sequenced by hybridization to complementary oligonucleotides, see, e.g., U.S. Pat. No. 5,202,231, to Drmanac et al. and, e.g., in Drmanac et al. (1989) Genomics 4:114–128. Also, chemical degradation sequencing methods are also well known and still in use and can be used in conjunction with the reactions described herein; see, Maxam and Gilbert (1980) in Grossman and Moldave (eds.) Academic Press, New York, *Methods in Enzymology* 65:499–560.

III. Apparatus

A. Microfluidic Device

In numerous embodiments of this invention, the reactions described herein are performed in a microfluidic device. As used herein, "microfluidic device" refers to an apparatus generally comprising a body comprising one or more microscale channels or chambers. In preferred embodiments, such channels are between about 0.1 and 500 $\mu$m in at least one cross-sectional dimension (e.g., width or depth). Typically the apparatus of this invention will comprise at least one main channel or chamber, wherein the reactions described herein will occur, as well as one or more side channels, fluidly connected to the at least one main channel or chamber. The side channels allow the introduction of, for example, test samples, buffers, pH altering chemicals, detectable markers, or other reagents into the main reaction channel or chamber. Such side channels may be fluidly connected to one or more sources of test samples, for example, or to one or more reservoirs of any of the reagents described herein. In addition, the side channels may be fluidly connected to additional elements included in the apparatus, such as detection zones or one or more receptacles for the collection of reaction products. Similarly, microscale devices of the invention optionally include separation matrixes for separation, purification, or enhanced analysis of PCR products. Microscale devices useful for practicing the methods of the invention include those having combined reaction regions and separation matrixes, e.g., as taught in by Mehta et al., Ser. No. 09/093,832.

In certain embodiments, one or more main channels are optionally and controllably connected to a network of channels. By controlling the fluid connection between the channels within the network, it is possible to control numerous aspects of the reaction itself, such as the number of cycles performed.

1. Thermocyclic Reactions

In numerous embodiments of this invention, the reaction comprises a thermocyclic reaction. In such embodiments, the main channel is desirably configured to alter the temperature of fluids passing through the channel. In preferred embodiments, the channel comprises multiple zones of varying temperatures, and the temperature of fluids within the channel is determined by the position of the fluid within the channel. Numerous means of controlling temperatures within a channel are known in the art, and preferred embodiments are described infra.

a) Zone Heating

In certain embodiments of this invention, the apparatus provides multiple temperature zones within a microfluidic device by zone heating. One such apparatus is described in Kopp et al. The apparatus described therein consists of a chip with three temperature zones, corresponding to denaturing, annealing, and primer extension temperatures. A channel fabricated into the chip passes through each zone multiple times to effect a 20 cycle PCR. By changing the flow rate of fluids through the chip, Kopp et al., were able to change the cycle time of the PCR. While devices used for the present invention can be similar to that described by Kopp et al., they typically differ in significant ways. First, the reactions performed by Kopp et al. were limited to 20 cycles, which was a fixed aspect of the chip used in their experiments. According to the present invention, reactions will comprise at least about 30 cycles, but more often as many as 50, 75, 100, or more cycles.

Suitable in the present invention is, e.g., the shortest cycle performed by Kopp et al., i.e. 4.5 seconds. However, as described supra, the reactions described in Kopp et al. were all limited to 20 cycles. Accordingly, as taught herein, the efficiency of that cycle was lower than usually obtained in PCR under standard conditions, and was not visible in their publication. The use of microfluidic chips comprising many more cycles than reported in Kopp et al is anticipated. In one embodiment, the methods of this invention can be performed in a microfluidic chip comprising at least 2 distinct temperature zones, and further comprising at least one channel that flows through each of the at least 2 distinct temperature zones to effect a PCR or other cyclic polymerase-mediated reaction comprising at least 30, 50, 100, or more cycles. Such channels can be fixed, so that each fluid flowing through the channel within a given chip undergoes the same number of cycles. Alternatively, the channel can comprise various microvalves, microshunts, and the like, so that manipulation of the channel itself can alter the number of cycles that a fluid flowing within the channel undergoes. In addition, the direction of fluid flow within the channels of the microfluidic devices can be altered, so that, for example, a fluid may be moved back and forth, from one temperature zone to another, multiple times to effect multiple cycles. Preferably, the means of manipulating the channels and fluid direction are controlled by a computer, as part of an integrated system, as described infra.

For example, reagents including template molecules, buffer, polymerase, primer molecules, and nucleotides are combined and introduced into a microscale channel fabricated into a body comprising at three temperature zones. The channel will pass multiple times through each of the temperature zones, so that the reagents pass sequentially through a denaturation zone (which zone is at least about 95°

C.), an annealing zone (which zone is between about 50° C. and about 65° C.), and an extension zone (which zone is about 72° C.). Often, the channel are fabricated so that, even with a constant flow rate, the reagents will spend more time in one or more of the zones as compared to the other zones, in one or more cycles of the reaction, e.g. the channel may comprise a longer path in one zone as compared to in another. Typically, the channel will pass through each of the zones at least about 35, 50, 75, or 100 or more times. The channel is fabricated to flow the reagents out of the body after the last of the cycles, whereupon the reagents or products can be collected. Alternatively, reagents or products can be detected directly in the channel, or flowed into secondary channels for fractionation (e.g., where the secondary channels comprise a separation matrix).

b) Joule Heating

Thermocycling for PCR and other thermocyclic applications can be conducted in microfluidic systems using joule heating. See, e.g. WO 98/17910. In brief, energy is provided to heat fluids, e.g., samples, analytes, buffers and reagents, in desired locations of the substrates in an efficient manner by application of electric current to fluids in microchannels. Thus, the present invention optionally uses power sources that pass electrical current through the fluid in a channel for heating purposes, as well as for material transport. In exemplary embodiments, the fluid passes through a channel of a desired cross-section (e.g., diameter) to enhance thermal transfer of energy from the current to the fluid. The channels can be formed on almost any type of substrate material such as, for example, amorphous materials (e.g., glass, plastic, silicon), composites, multi-layered materials, combinations thereof, and the like. In general, electric current passing through the fluid in a channel produces heat by dissipating energy through the electrical resistance of the fluid. Power dissipates as the current passes through the fluid and goes into the fluid as energy as a function of time to heat the fluid. The following mathematical expression generally describes a relationship between power, electrical current, and fluid resistance, i.e., POWER=$I^2$R where POWER=power dissipated in fluid; I=electric current passing through fluid; and R=electric resistance of fluid.

The above equation provides a relationship between power dissipated ("POWER") to current ("I") and resistance ("R"). In some of the embodiments, which are directed toward moving fluid in channels, e.g., to provide mixing, electrophoretic separation, or the like, a portion of the power goes into kinetic energy of moving the fluid through the channel. However, it is also possible to use a selected portion of the power to controllably heat fluid in a channel or selected channel regions. A channel region suitable for heating is often narrower or smaller in cross-section than other channel regions in the channel structure, as a smaller cross-section provides higher resistance in the fluid, which increases the temperature of the fluid as electric current passes through. Alternatively, the electric current is increased across the length of the channel by increased voltage, which also increases the amount of power dissipated into the fluid to correspondingly increase fluid temperature.

The introduction of electrical current into fluid causes heat (Joule heating). In the examples of fluid movement herein where thermal effects are not desired, the heating effect is minimal because, at the small currents employed, heat is rapidly dissipated into the chip itself. By substantially increasing the current across the channel, rapid temperature changes are induced that can be monitored by conductivity. At the same time, the fluid can be kept static in the channel by using alternating instead of direct current. Because nanoliter volumes of fluid have tiny thermal mass, transitions between temperatures can be extremely short. Oscillations between any two temperatures above 0° C. and below 100° C. in 100 milliseconds have been performed. Additional applications of joule heating to PCR methodologies are set forth in "Closed Loop Biochemical Analyzers" (WO 98/45481).

For example, reagents including template molecules, buffer, polymerase, primer molecules, and nucleotides are combined and introduced into a microscale channel fabricated with multiple regions wherein the current introduced into the channel, or the cross-sectional diameter of the channel, is modified to create a temperature of about 95° C. (comprising a denaturation zone), 50–65° C. (comprising an annealing zone), or about 72° C. (comprising an extension zone). The channel are configured so that each of these zones occurs sequentially, so that reagents passing through the channel will undergo denaturation, annealing, and extension, in that order. Often, the zones of the channel are configured so that one or more of the zones is longer than one or more of the other zones, so that one step of a reaction may be longer relative to the other steps, in one or more cycles of a reaction. Typically, the channel include at least about 35, 50, 75, or 100 or each of these zones. The channel will also often be fabricated to flow the reagents out of the body after the last of the cycles, whereupon the reagents can be collected.

2. Non-thermocyclic Reactions

In certain embodiments of this invention, the reactions described herein are performed at a single temperature. Such non-thermocyclic reactions are generally performed using reagents, such as chemical agents to change the pH of the solution in which the reaction is occurring. It will be appreciated that apparatus used for such embodiments comprise multiple means for effecting such chemical changes, including storing, introducing, mixing, and removing any chemicals used, for example, to effect the denaturation of the template. Example non-thermocyclic polymerase mediated reactions are taught in WO 98/45481.

In one such embodiment, a source of a base such as NaOH is fluidly connected to a reaction chamber in which the cyclic polymerase-mediated reaction occurs. Periodically, a fixed amount of a basic solution is added to the reactants. Preferably, the basic solution raises the pH of the solution to about pH 10–13 . After a set amount of time, a precise amount of an acidic solution such as HCl is added to the solution, thereby lowering the pH of the solution, e.g. to about pH 7–9. In certain embodiments, an additional aliquot of polymerase enzyme will also be added upon the lowering of the pH of the solution. In addition, desalting steps, e.g. to remove excess Na or Cl ions from the solution, may be included.

In alternative embodiments, a non-thermocyclic reaction occurs in a main channel of the apparatus, and pH altering chemicals such as NaOH or HCl are introduced at fixed positions into the channel. Often, such chemicals are stored in reservoirs fluidly connected to the main channel.

B. Additional Elements of the Apparatus

1. Source of Test Samples

Test samples (e.g. potentially containing a template nucleic acid) or test reagents can be loaded into microfluidic structures, e.g., by placing the reagent or sample in a well connected to a microfluidic channel network. The reagent or test sample is then flowed through the microchannel network, e.g., by pressure (positive or negative) or by electrokinesis.

Alternatively, test samples or reagents can be stored external to the microfluidic system in a system of wells, plates, or even as dried components stored on a surface. Thus, the integrated systems of the invention optionally include such external storage elements. In one aspect, the present invention includes a microwell plate (e.g., a 96, 384 or more well plate) having test samples or reagents stored within wells of the plate.

To introduce test samples or reagents into the microfluidic system, either pressure-based or electrokinetic approaches can be used. For example, electropipettors, or pressure-based pipettors (which can include one or multiple "sipper" channels) can be used to access wells or plates, or to re-hydrate soluble or suspendable dried components from dry storage media. A variety of access systems for coupling reagent storage and microfluidic systems are described in Knapp et al. "Closed Loop Biochemical Analyzers" WO 98/45481.

2. Detection Zone

The devices herein optionally include signal detectors, e.g., which detect fluorescence, phosphorescence, radioactivity, pH, charge, absorbance, luminescence, temperature, magnetism or the like. The detectors optionally monitor a plurality of signals from a plurality of products, either simultaneously or sequentially. For example, the detector can monitor a plurality of optical signals which correspond in position to products from a plurality of reactions. Example detectors include of photo multiplier tubes, a CCD array, a scanning detector or galvo-scann or the like. Reaction products which emit a detectable signal can be flowed past the detector, or, alternatively, the detector can move relative to a plurality of reaction products. The detector can include or be operably linked to a computer, e.g., which has software for converting detector signal information into nucleic acid sequence information, converting detector signal information into reaction kinetic information, etc.

In the case of fluorescent products, the detector will typically include a light source which produces light at an appropriate wavelength for activating the fluorescent product, as well as optics for directing the light source through the detection window to the products contained in the channel or chamber. The light source can be any number of light sources that provides an appropriate wavelength, including lasers, laser diodes and LEDs. Other light sources required for other detection systems. For example, broad band light sources are typically used in light scattering/transmissivity detection schemes, and the like. Typically, light selection parameters are well known to those of skill in the art.

The apparatus typically includes a detection window or zone at which a signal is monitored. This detection window typically includes a transparent cover allowing visual or optical observation and detection of the reaction products, e.g., observation of a colorometric, fluorometric or radioactive product. Detectors often detect a labeled compound, with typical labels including fluorographic, colorometric and radioactive components. Example detectors include spectrophotometers, photodiodes, microscopes, scintillation counters, cameras, film and the like, as well as combinations thereof. Examples of suitable detectors are widely available from a variety of commercial sources known to persons of skill. See, e.g., *The Photonics Design and Applications Handbook,* books 1, 2, 3 and 4, published annually by Laurin Publishing Co., Berkshire Common, P.O. Box 1146, Pittsfield, Mass. for common sources for optical components.

In alternative aspects, the detection system comprises non-optical detectors or sensors for detecting a particular characteristic of the products. Such sensors optionally include temperature, conductivity, potentiometric (pH, ions), amperometric (for compounds that can be oxidized or reduced, e.g., $O_2$, $H_2O_2$, $I_2$, oxidizable/reducible organic compounds, and the like). Many other suitable detection systems are known to one of skill.

The detector can exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

3. Receptacles for Product Isolation

The apparatus of this invention will also optionally include elements for collecting amplified reaction product, e.g. wells, channels, pipettors, membranes, 96 or 384-well plate, or the like. Of course, the reaction and product isolation regions of any microscale element can be integral, i.e., a single element can perform both functions.

In a preferred embodiment, an apparatus includes one or more receptacles for collecting the reaction volume following the last of the cycles of the reaction. In a particularly preferred embodiment, a plurality of receptacles will collect a plurality of reaction volumes resulting from a series of reactions performed in serial or in parallel. Typically, such a plurality of receptacles are included as part of an integrated system, as described below, and are controlled by a computer and/or robotic elements. Such receptacles will generally be microscale receptacles, appropriate for the very small reaction volumes typically used for the reactions described herein. In alternative aspects, the receptacles will collect reaction volumes following one or more cycles of the reactions of this invention other than the last cycle.

Typically, the reaction volumes are collected to allow downstream analysis or utilization of the reaction product. For example, the product may be detected using, e.g. electrophoresis, may be sequenced, cloned, or may be used, e.g. as a probe for the detection of other nucleic acids. Preferably, when such downstream steps are included, the integrated systems described herein will include means of collection and transferring reaction products for the downstream applications. In certain embodiments, the integrated systems will include means of performing the downstream applications as well.

C. Movement of Materials Within Microfluidic Systems

The microfluidic devices of this invention can include features such as fluid transport systems which direct fluid movement within a channel, e.g., fluid pressure sources for modulating fluid pressure in the channel, electrokinetic controllers for modulating voltage or current in the channel, gravity flow modulators, magnetic control elements for modulating a magnetic field within the channel, or combinations thereof. See, e.g. CLOSED LOOP BIOCHEMICAL ANALYZERS; WO 98/45481, and the references therein.

One method of achieving transport or movement of fluids through microfluidic channels is by electrokinetic material transport. "Electrokinetic material transport systems," as used herein, includes systems that transport and direct materials within a microchannel and/or chamber containing structure, through the application of electrical fields to the materials, thereby causing material movement through and among the channel and/or chambers, i.e., cations will move toward a negative electrode, while anions will move toward a positive electrode.

In general, electrokinetic material transport and direction systems include those systems that rely upon the electrophoretic mobility of charged species within the electric field applied to the structure. Such systems are more particularly referred to as electrophoretic material transport systems. A variety of electrokinetic controllers are described, e.g., in Ramsey WO 96/04547, Parce et al. WO 98/46438 and Dubrow et al., WO 98/49548, as well as a variety of other references noted herein.

Fluid flow can also be regulated by pressure based mechanisms such as those based upon fluid displacement, e.g., using a piston, pressure diaphragm vacuum pump or probe to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, i.e., a plunger fitted into a material reservoir, for forcing the material along through the channel. Alternatively, the apparatus includes a pressure or vacuum source to effect fluid movement through the channel. Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

Hydrostatic, wicking and capillary forces can also be used to provide for fluid flow. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., filed Feb. 5, 1999.

In an alternate embodiment, microfluidic systems can be incorporated into centrifuge rotor devices, which are spun in a centrifuge. Fluids and particles travel through the device due to gravitational and centripetal/centrifugal forces.

D. Reactions Using Microscale Arrays

The present invention can also be practiced using microfluidic arrays. Such arrays are described in detail in patent application MANIPULATION OF MICROPARTICLES IN MICROFLUIDIC SYSTEMS, filed Feb. 23, 1999, by Mehta et al. The array components can be mobile or fixed. They can also be of a selected type or type switchable, and can incorporate any of a wide variety of chemical or biochemical components. The arrays can be components of integrated systems.

Methods of performing a plurality of cyclic polymerase-mediated reactions in a microscale device comprising an array are an aspect of this invention. In the methods, an array within a microfluidic system (e.g., having a body structure with a microscale interior cavity, etc. as described above) is provided. One or more liquid reagents, comprising, e.g., polymerase, buffer, nucleotides, or primers, is flowed into the interior cavity and into contact with particle sets of the array. Often, template molecules are incorporated into the particles of an array. Such template molecules may comprise the same sequence, or may comprise a multitude of sequences to allow the concurrent amplification of numerous sequences.

Optionally, one or more of the plurality of sets of particles of the array (or the entire array or a substantial portion of) is moved through a main channel of a microfluidic device, wherein the channel comprises multiple distinct temperature zones. In addition, the particles can be flowed into or through an intersection of at least two channels present in a microfluidic system. Mixing can occur in the intersections of channels, or within chambers, channels, wells, reservoirs, or the like. Thus, in the methods of the invention, at least one of the plurality of sets of particles can be moved through at least one of the at least two channels into an intersection of the at least two channels, while (separately or simultaneously) flowing a liquid reagent (e.g. polymerase, primers, nucleotides) through a second of the at least two channels into the channel intersection, where the liquid reagent flows into contact with at least one set of particles of the array. In one aspect, the cavity comprises a main channel having a plurality of intersecting side channels, forming a plurality of channel intersections between the main channel and each of the intersecting side channels. The methods optionally include transporting at least one of the plurality of sets of particles in the main channel into at least two of the plurality of channel intersections.

Similarly, in one aspect, the method includes transporting at least one fluidic reagent through at least one of the side channels into at least one of the plurality of channel intersections, where the reagent flows into at least one of the plurality of sets of particles in the main channel.

Methods also optionally include moving particles (or reagents) into the interior cavity. For example, in one embodiment, the interior cavity has a broad channel with narrow channels within the broad channel. The narrow channels are deeper in at least one dimension than the broad channel. A plurality of sets of particles are transported into one or more of the narrow channels to form the array. Optionally, a liquid reagent is also (subsequently or previously) transported through the broad channel and the narrow channel and into contact with the plurality of sets of particles. Exemplar liquid reagents include those described above such as buffers, pH-altering chemicals, polymerases, primers, nucleotides including detectable nucleotides, etc.

Methods of contacting samples and reagents in a microfluidic system are also provided. For example, a plurality of members of a particle array which includes a plurality of template molecules is transported to a selected location within the microfluidic system. Simultaneously, separately or sequentially, reagents are also transported within the microfluidic system such that members of the particle array and the reagents are contacted. Members of the particle array and the reagents are optionally repeatedly transported sequentially or simultaneously within the microfluidic system. In microfluidic systems having one or more emission detectors, the method optionally includes transporting the plurality of particle members past the one or more emission detectors, before, during, or after contacting the plurality of particle members with one or more of the reagents.

IV. Integrated Systems

The apparatus described herein are often incorporated into integrated systems comprising additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

A. Controllers

A variety of controlling instrumentation is optionally utilized in conjunction with the microfluidic devices described above, for controlling the transport and direction of fluids and/or materials within the devices of the present invention, e.g., by pressure-based or electrokinetic control.

For example, in many cases, fluid transport and direction are controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. In such systems, fluid direction is often accomplished through the incorporation of microfabricated valves, which restrict fluid flow in a controllable manner. See, e.g., U.S. Pat. No. 5,171,132.

As noted above, the systems described herein can also utilize electrokinetic material direction and transport systems. As such, the controller systems for use in conjunction with the microfluidic devices typically include an electrical power supply and circuitry for concurrently delivering appropriate voltages to a plurality of electrodes that are placed in electrical contact with the fluids contained within the microfluidic devices. Examples of particularly preferred electrical controllers include those described in, e.g., published PCT application WO 98/00707 and in U.S. Pat. No. 5,800,690. In brief, the controller uses electric current control in the microfluidic system. The electrical current flow at a given electrode is directly related to the ionic flow along the channel(s) connecting the reservoir in which the electrode is placed. This is in contrast to the requirement of determining voltages at various nodes along the channel in a voltage control system. Thus the voltages at the electrodes of the microfluidic system are set responsive to the electric currents flowing through the various electrodes of the system. This current control is less susceptible to dimensional variations in the process of creating the microfluidic system in the device itself. Current control permits far easier operations for pumping, valving, dispensing, mixing and concentrating subject materials and buffer fluids in a complex microfluidic system. Current control is also preferred for moderating temperature effects (e.g., joule heating) within the channels. Flow can also be driven by capillary or wicking forces, e.g. as described in "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., filed Feb. 5, 1999.

Typically, the controller systems are appropriately configured to receive a microfluidic device as described herein. In particular, the controller and/or detector (as described in greater detail, below), includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for electrokinetic injection or withdrawal of material downstream of the region of interest to control an upstream flow rate.

B. Computers

As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring of materials in the channels, so that flow rate and velocity may be determined. Additionally the software is optionally used to control electrokinetic injection or withdrawal of material. The electrokinetic or withdrawal is used to modulate the flow rate as described above.

V. Kits

Generally, the reagents and devices described herein are packaged to include many if not all of the necessary components for performing the reactions described herein. For example, the kits can include any of templates, polymerases, primers, buffers and other chemical agents, nucleotides, sample materials, control materials, devices, or the like. Such kits also typically include appropriate instructions for using the devices and/or reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (of course, in one preferred embodiment, the device itself comprises a pipettor element, such as an electropipettor for introducing material into channels and chambers within the device). In the former case, such kits typically include a microfluidic device with necessary reagents predisposed in the channels/chambers of the device. The kits can optionally include reagents in the absence of any devices. Generally, reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

The discussion above is generally applicable to the aspects and embodiments of the invention described below.

Moreover, modifications can be made to the method and apparatus described herein without departing from the spirit and scope of the invention as claimed, and the invention can be put to a number of different uses including the following:

The use of a cyclic polymerase-mediated reaction including a high number of short cycles to amplify one or more nucleic acids.

The use of a microfluidic system with at least one microscale channel, which channel confers multiple temperature changes on any fluids therein, to perform a cyclic polymerase-mediated reaction.

The use of a microfluidic system with at least one microscale chamber and with a system to control the movement of fluids, to sequentially alter the conditions, e.g. pH, of a reaction solution, to perform a non-thermocyclic cyclic polymerase-mediated reaction.

The use of an array in a microfluidic device as described herein to perform a cyclic polymerase-mediated reaction.

An assay utilizing a use of any one of the microfluidic systems or substrates described herein.

Unless indicated otherwise, concentration of a particular component in a solution optionally refers to relative quantity of a component in to be admixed, rather than to a quantity of the material in an actual solution. One of skill will recognize that certain components alter their form when added to a solution of interest (e.g., salts can dissociate into ions, etc.).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted.

What is claimed is:

1. A method of performing a cyclic polymerase-mediated reaction, the method comprising:

incubating a polymerase, a plurality of template molecules, and a plurality of primer molecules for a first time ($t_1$), wherein $t_1 \leq 0.5(t_2)$, wherein $t_2$ is the time required for the duplication of at least 90% of the plurality of template molecules when said primer molecules and said polymerase are present in non-rate limiting amounts; and repeating the incubation of said polymerase, said plurality of template molecules, and said plurality of primer molecules, for time $t_1$, for a number of cycles, $x_1$, wherein $x_1$ is greater than the number of cycles required to produce a detectable amount of product when said polymerase, said plurality of template molecules, and said plurality of primer molecules are incubated for time $t_2$, wherein the total amount of time required to generate a detectable amount of product using said increased number of said reduced-time cycles is less than the total amount of time required to generate a detectable amount of product sing the standard number of full-time cycles.

2. The method of claim 1, wherein said cyclic polymerase-mediated reaction is a PCR.

3. The method of claim 1, wherein said incubation is performed in a microfluidic device comprising at least one microscale channel.

4. The method of claim 1, said reaction comprising denaturation of the plurality of template molecules, wherein the plurality of template molecules is denatured to provide a plurality of single stranded template molecules.

5. The method of claim 4, wherein the denaturation comprises incubation of said template molecules with a base.

6. The method of claim 1, said reaction comprising hybridization of the plurality of primer molecules to the plurality of template molecules.

7. The method of claim 6, wherein the hybridization of the plurality of primer molecules to the plurality of template molecules and the extension of the primer molecules are performed simultaneously.

8. The method of claim 1, wherein the reaction is a thermocyclic reaction.

9. The method of claim 1, wherein said time $t_1$ is less than about 2 seconds.

10. The method of claim 1, wherein said time $t_1$ is less than about 1 second.

11. The method of claim 1, wherein the percentage of said plurality of templates that is duplicated when incubated with said polymerase and said plurality of primers for time $t_1$ is less than about 70%.

12. The method of claim 1, wherein the percentage of said plurality of templates that is duplicated when incubated with said polymerase and said plurality of primers for time $t_1$ is less than about 50%.

13. The method of claim 1, wherein the percentage of said plurality of templates that is duplicated when incubated with said polymerase and said plurality of primers for time $t_1$ is less than about 30%.

14. The method of claim 1, wherein the percentage of said plurality of templates that is duplicated when incubated with said polymerase and said plurality of primers for time $t_1$ is less than about 10%.

15. The method of claim 1, wherein the percentage of said plurality of templates that is duplicated when incubated with said polymerase and said plurality of primers for time $t_1$ is less than about 5%.

16. The method of claim 1, wherein said detectable amount of product is at least about 100 ng.

17. The method of claim 1, wherein said detectable amount of product is at least about 10 ng.

18. The method of claim 1, wherein said detectable amount of product is at least about 0.01 pmoles.

19. The method of claim 1, wherein said detectable amount of product is at least about 0.1 pmoles.

20. The method of claim 1, wherein said detectable amount of product is at least about 1 pmole.

21. The method of claim 1, wherein said detectable amount of product is at least about 10 pmoles.

22. The method of claim 1, wherein said template is derived from a biological source selected from: humans, mammals, vertebrates, insects, bacteria, fungi, plants, and viruses.

23. The method of claim 1, wherein the template comprises a target nucleic acid, and the method further comprises detecting a product of the incubation of the polymerase, the plurality of primer molecules, and the target nucleic acid.

24. The method of claim 1, wherein said number ($x_1$) of cycles is at least about 25.

25. The method of claim 1, wherein said number ($x_1$) of cycles is at least about 50.

26. The method of claim 1, wherein said number ($x_1$) of cycles is at least about 100.

27. The method of claim 1, wherein said number ($x_1$) of cycles is at least about 200.

28. The method of claim 1, wherein said number ($x_1$) of cycles is at least about 400.

29. The method of claim 1, wherein a detectable marker is incorporated into said product during said incubation.

30. The method of claim 1, wherein a reagent to allow the sequencing of the product is incorporated into the product during at least one cycle of the incubation.

31. The method of claim 30, the reagent comprising a dideoxynucleotide.

32. The method of claim 30, the reagent comprising a boronated nuclease resistant nucleotide.

33. The method of claim 1, further comprising a separation step wherein the product is isolated following said number ($x_1$) of cycles.

34. A method of performing a PCR, comprising:
(i) performing the PCR using a reduced-time cycle, which reduced-time cycle is shorter in duration than a full-time cycle, which full-time cycle is sufficient in duration for the duplication of at least 90% of the templates present in said full-time cycle; and
(ii) using an increased number of said reduced-time cycles compared to a standard number of full-time cycles, which standard number of full-time cycles is sufficient to generate a detectable amount of product, wherein the total amount of time required to generate a detectable amount of product using said increased number of said reduced-time cycles is less than the total amount of time required to generate a detectable amount of product using the standard number of full-time cycles.

35. The method of claim 34, wherein said increased number of said reduced-time cycles generates a detectable amount of product.

36. The method of claim 34, comprising an extension step of about 2 seconds or less.

37. The method of claim 34, comprising an extension step of about 1 second or less.

38. The method of claim 34, comprising an extension step of about 0.5 seconds or less.

39. The method of claim 35, wherein the detectable amount of product is at least about 100 ng of DNA.

40. The method of claim 35, wherein the detectable amount of product is at least about 10 ng of DNA.

41. The method of claim 35, wherein the detectable amount of product is at least about 0.01 pmoles of DNA.

42. The method of claim 35, wherein the detectable amount of product is at least about 0.1 pmoles of DNA.

43. The method of claim 35, wherein the detectable amount of product is at least about 1 pmole of DNA.

44. The method of claim 35, wherein the detectable amount of product is at least about 10 pmoles of DNA.

45. The method of claim 34, wherein the PCR is performed in a microfluidic device comprising at least one microscale channel.

46. The method of claim 34, the PCR comprising denaturation of the templates, wherein the templates are denatured to provide a plurality of single stranded templates.

47. The method of claim 46, the denaturation comprising incubation of the templates with a base.

48. The method of claim 34, the PCR comprising hybridization of a plurality of primer molecules to the templates.

49. The method of claim 48, wherein the hybridization of the plurality of primer molecules to the templates is performed simultaneously with the reduced-time cycle.

50. The method of claim 34, wherein the duration of one cycle of the PCR is less than about 4.5 seconds.

51. The method of claim 34, wherein the duration of one cycle of the PCR is less than about 2 seconds.

52. The method of claim 34, wherein the duration of one cycle of the PCR is less than about 1 second.

53. The method of claim 34, wherein less than about 70% of the templates are duplicated in each cycle of the PCR.

54. The method of claim 34, wherein less than about 50% of the templates are duplicated in each cycle of the PCR.

55. The method of claim 34, wherein less than about 30% of the templates are duplicated in each cycle of the PCR.

56. The method of claim 34, wherein less than about 10% of the templates are duplicated in each cycle of the PCR.

57. The method of claim 34, wherein less than about 5% of the templates are duplicated in each cycle of the PCR.

58. The method of claim 34, wherein the PCR comprises at least about 25 cycles.

59. The method of claim 34, wherein the PCR comprises at least about 50 cycles.

60. The method of claim 34, wherein the PCR comprises at least about 100 cycles.

61. The method of claim 34, wherein the PCR comprises at least about 200 cycles.

62. The method of claim 34, wherein the PCR comprises at least about 400 cycles.

63. The method of claim 34, wherein the PCR is a thermocyclic reaction.

64. The method of claim 34, wherein the templates are derived from a biological source selected from: humans, mammals, vertebrates, insects, bacteria, fungi, plants, and viruses.

65. The method of claim 34, wherein the templates comprise target nucleic acids, and the method further comprises detecting a product of the duplication of the target nucleic acids.

66. The method of claim 34, wherein a detectable marker is incorporated into the product during the incubation.

67. The method of claim 34, wherein a reagent to allow the sequencing of the product is incorporated into the product during at least one cycle of the incubation.

68. The method of claim 67, the reagent comprising a dideoxynucleotide.

69. The method of claim 68, the reagent comprising a boronated nuclease resistant nucleotide.

70. The method of claim 34, further comprising a separation step wherein the product is isolated following the increased number of reduced time cycles.

71. A method of amplifying a template, the method comprising incubating the template with at least one complementary primer and a polymerase, wherein the incubation comprises:
(i) denaturing the template to provide a single stranded template;
(ii) hybridizing the at least one complementary primer and the single stranded template; and
(iii) extending the resulting hybridized primer with the polymerase;
wherein the total time for the denaturing, hybridizing, and extending is about 6 seconds or less; and
(iv) repeating steps (i), (ii), and (iii) until a detectable amount of product is produced, wherein the total amount of time required to generate a detectable amount of product is less than the total amount of time required to generate a detectable amount of product using the standard number of full-time cycles.

72. The method of claim 71, the method comprising a PCR.

73. The method of claim 71, wherein the incubation is performed in a microfluidic device.

74. The method of claim 71, wherein the detectable amount of product is at least about 10 ng of product.

75. The method of claim 71, wherein the detectable amount of product is at least about 100 ng of product.

76. The method of claim 71, wherein the detectable amount of product is at least about 0.01 pmoles of product.

77. The method of claim 71, wherein the detectable amount of product is at least about 0.1 pmoles of product.

78. The method of claim 71, wherein the detectable amount of product is at least about 1 pmole of product.

79. The method of claim 71, wherein the detectable amount of product is at least about 10 pmoles of product.

80. The method of claim 71, wherein steps (ii) and (iii) are performed simultaneously.

81. The method of claim 71, the method comprising incubation at a plurality of temperatures.

82. The method of claim 71, wherein the polymerase is selected from: thermostable polymerase, *E. coli* DNA pol I, Klenow fragment, and T7 DNA polymerase.

83. The method of claim 71, wherein the denaturing comprises incubating the template with a base.

84. The method of claim 71, wherein the total time for the denaturing, hybridizing, and extending is about 4.5 seconds or less.

85. The method of claim 71, wherein the total time for the denaturing, hybridizing, and extending is about 2 seconds or less.

86. The method of claim 71, wherein the total time for the denaturing, hybridizing, and extending is about 1 second or less.

87. The method of claim 71, wherein the percentage of the templates that are duplicated in step (iii) is less than about 70%.

88. The method of claim 71, wherein the percentage of the templates that is duplicated in step (iii) is less than about 50%.

89. The method of claim 71, wherein the percentage of the templates that is duplicated in step (iii) is less than about 30%.

90. The method of claim 71, wherein the percentage of the templates that is duplicated in step (iii) is less than about 10%.

91. The method of claim 71, wherein the percentage of the templates that is duplicated in step (iii) is less than about 5%.

92. The method of claim 71, wherein the template is derived from a biological source selected from: humans, mammals, vertebrates, insects, bacteria, fungi, plants, and viruses.

93. The method of claim 71, wherein the template comprises a target nucleic acid, and the method further comprises detecting a product of the incubation of the polymerase, the complementary primer, and the target nucleic acid.

94. The method of claim 71, wherein steps (i), (ii), and (iii) are repeated at least about 25 times.

95. The method of claim 71, wherein steps (i), (ii), and (iii) are repeated at least about 50 times.

96. The method of claim 71, wherein steps (i), (ii), and (iii) are repeated at least about 100 times.

97. The method of claim 71, wherein steps (i), (ii), and (iii) are repeated at least about 200 times.

98. The method of claim 71, wherein steps (i), (ii), and (iii) are repeated at least about 400 times.

99. The method of claim 71, wherein a detectable marker is incorporated into the product during at least one execution of step (iii).

100. The method of claim 71, wherein a reagent to allow the sequencing of the product is incorporated into the product during at least one execution of step (iii).

101. The method of claim 100, the reagent comprising a dideoxynucleotide.

102. The method of claim 100, the reagent comprising a boronated nuclease resistant nucleotide.

103. The method of claim 71, further comprising a separation step wherein the amplified product is isolated.

104. The method of claim 71, wherein the template is at least about 175 base pairs.

* * * * *

UNITED STATES PATENT AND TRADEMARK OFFICE
CERTIFICATE OF CORRECTION

PATENT NO.     : 6,303,343 B1
DATED          : October 16, 2001
INVENTOR(S)    : Anne R. Kopf-Sill et al.

It is certified that error appears in the above-identified patent and that said Letters Patent is hereby corrected as shown below:

Column 29, claim 1,
Line 51, "sing" should be -- using --.

Column 32, claim 69,
Line 30, "68" should be -- 67 --.

Signed and Sealed this

Ninth Day of April, 2002

Attest:

JAMES E. ROGAN
Attesting Officer    Director of the United States Patent and Trademark Office

UNITED STATES PATENT AND TRADEMARK OFFICE
CERTIFICATE OF CORRECTION

PATENT NO.    : 6,303,343 B1                                           Page 1 of 1
DATED         : October 16, 2001
INVENTOR(S)   : Kopf-Sill It is certified that error appears in the above-identified patent and that said Letters Patent is hereby corrected as shown below:

<u>Column 1,</u>
Line 11, please delete "Not Applicable" and insert -- The present invention was made with government funding from the United States National Institute of Standards and Technology (NIST), through the Advanced Technology Program (ATP) under Grant No. 70NANB8H4000, and the United States government may have certain rights in the invention. --

Signed and Sealed this

Fifth Day of August, 2003

JAMES E. ROGAN
*Director of the United States Patent and Trademark Office*